US012329688B2

(12) United States Patent
Malov

(10) Patent No.: US 12,329,688 B2
(45) Date of Patent: Jun. 17, 2025

(54) WELDING SHIELD WITH ARTIFICIAL INTELLIGENCE-CONTROLLED DISPLAY

(71) Applicant: Alexey Victorovich Malov, St. Petersburg (RU)

(72) Inventor: Alexey Victorovich Malov, St. Petersburg (RU)

(*) Notice: Subject to any disclaimer, the term of this patent is extended or adjusted under 35 U.S.C. 154(b) by 924 days.

(21) Appl. No.: 17/496,621

(22) Filed: Oct. 7, 2021

(65) Prior Publication Data

US 2022/0125642 A1    Apr. 28, 2022

(30) Foreign Application Priority Data

Oct. 24, 2020    (RU) ................................ 2020134919

(51) Int. Cl.
*A61F 9/06*    (2006.01)
*B23K 9/095*    (2006.01)
(Continued)

(52) U.S. Cl.
CPC .............. *A61F 9/06* (2013.01); *B23K 9/0953* (2013.01); *B23K 9/0956* (2013.01); *B23K 9/322* (2013.01);
(Continued)

(58) Field of Classification Search
CPC ........ G06V 10/82; G06V 20/46; G06V 20/20; G06N 3/08; G06N 3/045; B23K 9/322; B23K 9/0953; B23K 31/006; B23K 9/0956; G02B 27/0172; G02B 27/0101; G02B 27/0176; G02B 2027/014;
(Continued)

(56) References Cited

U.S. PATENT DOCUMENTS 9,767,712 B2 *    9/2017    Postlethwaite ........ G09B 19/24
9,836,987 B2 *    12/2017    Postlethwaite ........ G09B 19/24
(Continued)

FOREIGN PATENT DOCUMENTS

CN    106569335 A *    4/2017    ........... H04N 9/3141
CN    109434251 A *    3/2019    ........... B23K 9/1274
(Continued)

OTHER PUBLICATIONS

CN 109434251 A Translation (Year: 2019).*
(Continued)

*Primary Examiner* — Eric S Stapleton
(74) *Attorney, Agent, or Firm* — Bardmesser Law Group

(57) ABSTRACT

Welder's shield with AI includes a frame for mounting on a user's head; a camera mounted on the frame and directed forward toward welding zone, to obtain images of welding zone as video data; a display on an inner side of the frame; an optical device to enable the user to see the display; battery; processor receiving a video data from the camera; the processor running an AI application to process the video data; the processor displaying images on the display based on output of the AI application; the artificial intelligence application receiving the video data and detecting a welding arc in the welding zone using a pattern recognition algorithm; and the AI application modifying the video data to reduce an intensity of the welding arc in the images that are to be displayed on the display, without reducing an intensity of the rest of the images.

15 Claims, 3 Drawing Sheets

(51) Int. Cl.
*B23K 9/32* (2006.01)
*G02B 27/01* (2006.01)
*G06N 3/08* (2023.01)
*G06V 20/40* (2022.01)
*H04N 5/58* (2006.01)

(52) U.S. Cl.
CPC ..... *G02B 27/0101* (2013.01); *G02B 27/0172* (2013.01); *G02B 27/0176* (2013.01); *G06N 3/08* (2013.01); *G06V 20/46* (2022.01); *H04N 5/58* (2013.01); *G02B 2027/0138* (2013.01)

(58) Field of Classification Search
CPC .... G02B 2027/0141; G02B 2027/0138; A61F 9/06; H04N 5/58
USPC ...................................................... 219/130.1
See application file for complete search history.

(56) References Cited

U.S. PATENT DOCUMENTS

| | | | | |
|---|---|---|---|---|
| 10,773,329 | B2 * | 9/2020 | Beeson | B23K 9/0956 |
| 2009/0231423 | A1 * | 9/2009 | Becker | H04N 7/183 |
| | | | | 386/326 |
| 2014/0017642 | A1 * | 1/2014 | Postlethwaite | G09B 19/24 |
| | | | | 434/234 |
| 2015/0235565 | A1 * | 8/2015 | Postlethwaite | G09B 5/06 |
| | | | | 434/234 |
| 2015/0320601 | A1 * | 11/2015 | Gregg | G06T 1/0007 |
| | | | | 2/8.2 |
| 2016/0033159 | A1 * | 2/2016 | Rockwood | F24F 13/04 |
| | | | | 454/261 |
| 2016/0207134 | A1 * | 7/2016 | Beeson | G06F 3/017 |
| 2017/0032358 | A1 * | 2/2017 | Gibson | G06Q 20/3226 |
| 2017/0227766 | A1 | 8/2017 | Patel et al. | |
| 2019/0160578 | A1 * | 5/2019 | Nakagawa | B23K 9/067 |
| 2019/0321905 | A1 * | 10/2019 | Wang | B23K 9/167 |
| 2020/0374510 | A1 * | 11/2020 | Berends | B23K 9/32 |

FOREIGN PATENT DOCUMENTS

| | | | |
|---|---|---|---|
| CN | 109949346 A * | 6/2019 | |
| CN | 111653136 A * | 9/2020 | |
| RU | 2457815 C1 | 8/2012 | |
| RU | 2715116 C1 | 2/2020 | |
| WO | 2016/089545 A1 | 9/2016 | |
| WO | 2016144744 A1 | 9/2016 | |

OTHER PUBLICATIONS

CN 106569335 A Translation (Year: 2017).*
CN 109949346 A Translation (Year: 2019).*
CN 111653136 A Translation (Year: 2020).*
Search report in RU 2020134919, dated Sep. 9, 2021.
Search report in EP 21204058.8-1016, dated Mar. 3, 2022.
Park Je-Kang et al: "Convolutional Neural Network Based Surface Inspection System for Non-patterned Welding Defects", International Journal of Precision Engineering and Manufacturing, Korean Society for Precision Engineering, Springer, vol. 20, No. 3, Feb. 22, 2019 (Feb. 22, 2019), pp. 363-374, XP036741899, ISSN: 2234-7593, 001: 10.1 007/S12541-019-00074-4 retrieved on Feb. 22, 2019].
B. Hillers, D.Aiteanull, P. Tschirner, M. Park, AGraser, B. Balazs, L. Schmid, Terebes: Welding Helmet with AR capabilities, Jan. 2004.
Yeong-Do Park et al., The Design of an Intelligent Augmented Reality Welder Training System, International Journal of Engineering Research and Technology, vol. 6, Issue 02, Feb. 2017.
Kenneth Fast et al., Virtual Training for Welding, Proceedings of the Third IEEE and ACM International Symposium on Mixed and Augrnented Reality (ISMAR 2004).

* cited by examiner

WELDING SHIELD WITH ARTIFICIAL INTELLIGENCE-CONTROLLED DISPLAY

CROSS REFERENCE TO RELATED APPLICATIONS

This application claims priority to Russian Patent Application No. 2020134919, filed on Oct. 24, 2020, incorporated herein by reference.

TECHNICAL FIELD

The present disclosure relates to the field of welding production and can be used to protect a person during welding. More specifically, the present disclosure relates to personal protective equipment that has artificial intelligence.

BACKGROUND OF THE RELATED ART

A curved auto-darkening light filter (RU patent No. 2719306, priority dated Dec. 13, 2012) is known. The light filter changes its state from light-transmitting to shade mode under the influence of incident light. The auto-darkening light filter is manufactured by a method based on forming a liquid crystal cell. The invention provides a reduction in weight and an expansion of the field of view for the user.

The disadvantages of welding shields based on this device, as well as other well-known commercial welding shields with auto-darkening light filters (lincolnelectric.com/en/Products/Safety/Head-Face-and-Eye/Welding-Helmets-and-Accessories/VIKING-3350-Series) are listed below:

When voltaic arc light is detected, the light filter enters shade mode for protection the welder from dazzle. In this mode voltaic arc area and a small area around it remains light, but not dazzling, and the rest of the area is darkened. Thus, only a small area voltaic arc the arc is clearly visible. The welder does not see everything that is around. In such case, for example, it is difficult to estimate when the end of the soldering line will be reached, what part of the soldering line is done. You need to rely on visual memory and evaluate intuitively, or temporarily stop welding to get the filters out of shade mode.

Also, in a shade mode, the arc area and a small area around it remains light, while the rest are darkened. Such a regime is unnatural for the eyes and leads to increased fatigue.

The closest technical solution is a shield for welding (RU patent No. 2457815, priority dated Apr. 5, 2011), which contains an actuator attached to it, a viewing slot and a holder with a light filter installed with the ability to close and open the slot by means of a mechanism, a spring, mouthpiece and air duct. The end of the mouthpiece is located near the lips. The actuator is made in the form of a bellows with a stem. The air duct is fixedly fixed on the faceplate and is connected at one end to the mouthpiece, and at the other end to the bellows, the stem of which is connected to the light filter holder rotating around the axis. The spring is fixed on the holder and face shield.

The disadvantages of this shield include the disadvantages listed for the invention described previously. Another disadvantage is the need for the welder to control the movement of the light filter using the pressure in the mouth.

SUMMARY OF THE INVENTION

In one aspect, there is provided a welder's shield with artificial intelligence including a frame for mounting on a user's head; a camera mounted on the frame and directed forward toward a welding zone, so as to obtain images of the welding zone as video data; a display on an inner side of the frame; an optical device to enable the user to see the display; a processor coupled to a memory; a battery providing power to the processor, the display and the camera; the processor receiving a video data from the camera; the processor running an artificial intelligence application to process the video data from the video camera; the processor displaying images on the display based on output of the artificial intelligence application; the artificial intelligence application receiving the video data and detecting a welding arc in the welding zone using a pattern recognition algorithm; and the artificial intelligence application modifying the video data to reduce an intensity of the welding arc in the images that are to be displayed on the display, without reducing an intensity of a remainder of objects in the images being displayed.

Optionally, the video data is provided from the video camera to the processor using a wireless interface. Optionally, the video data is provided from the video camera to the processor using a high definition multimedia wire interface. Optionally, the video data is provided from the processor to the display using a high definition multimedia wire interface. Optionally, the video data is provided to the processor using a universal serial bus wire interface. Optionally, the artificial intelligence application processes the video data on a frame by frame basis. Optionally, the pattern recognition algorithm uses a histogram of oriented gradients for detecting the welding arc. Optionally, the pattern recognition algorithm uses a convolutional neural network for detecting the welding arc. Optionally, the recognition algorithm uses prepared pre-trained model based on neural network or histogram of oriented gradients, and wherein the model has an object corresponding to the welding arc. Optionally, the artificial intelligence application provides for adjustment of a photosensitivity of the video camera based on a brightness of the welding arc. Optionally, the artificial intelligence application provides for adjustment of a photosensitivity of the video camera based on a brightness of a surrounding environment. Optionally, a graphical processing unit is coupled to the processor for processing the images.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE ATTACHED FIGURES

The accompanying drawings, which are included to provide a further understanding of the invention and are incorporated in and constitute a part of this specification, illustrate embodiments of the invention and, together with the description, serve to explain the principles of the invention.

DETAILED DESCRIPTION OF THE PREFERRED EMBODIMENTS

Figure 1:
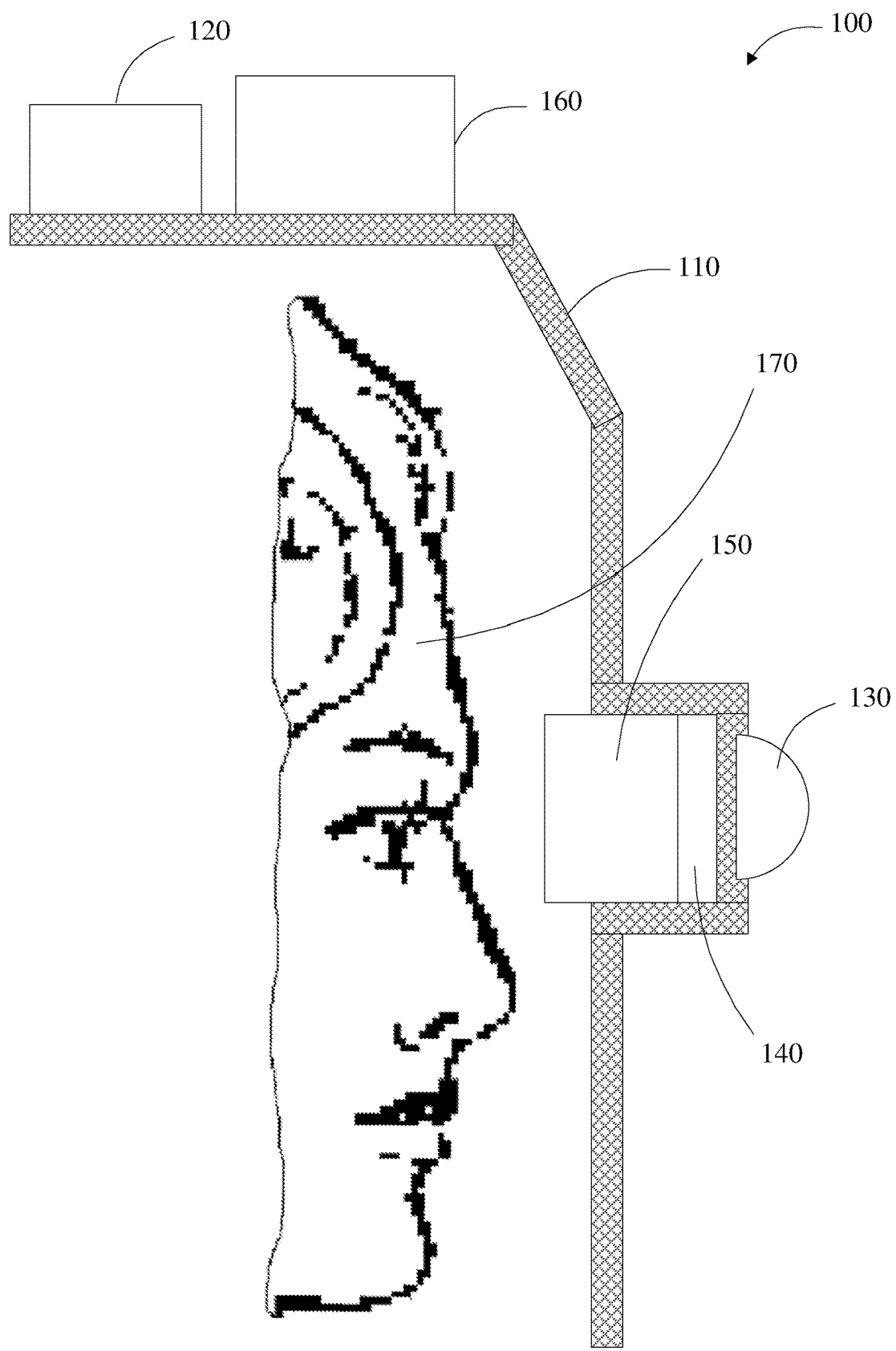
FIG. 1 illustrates a welding shield that includes a power source, digital video cameras, display and computing device, in accordance with this disclosure.

Reference will now be made in detail to the preferred embodiments of the present invention, examples of which are illustrated in the accompanying drawings.

The technical result is an improvement in working conditions, an increase in work productivity.

The task is solved as follows. The welding shield is a head-mounted device comprising:
- (1) autonomous power source, for example, an accumulator battery
- (2) One or several digital video cameras on the outer side of the shield. Above-mentioned digital video cameras directed in the direction of the welder's direct gaze, allowing to obtain an image with an angle of coverage of at least a direct view of the welder. Digital video cameras above designed for stable operation in the presence of bright light sources.
- (3) display on the inside side of the shield
- (4) an optical system located in front of the display and allowing the welder to adjust the image to the individual characteristics of the welder's vision
- (4) a computing device comprising permanent storage device, random access memory, one or more computer processors, and an installed general-purpose operating system. Also, the data computing device has interfaces to which the above-mentioned video cameras and display are connected. The computing device also contains installed and configured software capable of:
  - (a) to receive data from above-mentioned video cameras
  - (b) to run an artificial intelligence application on execution to process data from video cameras
  - (c) to send data from video cameras to an artificial intelligence application
  - (d) to display data received from an artificial intelligence application on the display
- (4) an artificial intelligence application running on an above-mentioned computing device capable of:
  - (a) to receive video data received from video cameras
  - (b) to detect the appearance of a welding arc using pattern recognition algorithms, change the resulting image and instead of the welding arc put instead of the welding arc an illuminated spot that is comfortable for the eye
  - (c) to send the processed image for display
  - (d) to provide processing of video data with a delay visually imperceptible to humans
  - (e) to provide adjustment of the video camera's light sensitivity based not on the brightness of the arc, but on the brightness comfortable for the welder's eye From the prior art, no solutions have been identified that have features that coincide with the distinctive features of the claimed invention and have the same effect as they do on the technical result, which consists in improving working conditions, increasing labor productivity. These distinctive features allow achieving the following advantages over the prototype:
- (1) Not only a small area around the welding arc is clearly visible, but the entire area of the line of sight.
- (2) The entire screen is evenly illuminated and not one bright spot in the welding arc area and a small area nearby. This mode is natural for the organs of vision and reduces fatigue.
- (3) There is no need for the welder to control the movement of the filter using the pressure in the mouth.

The welder's shield works as follows: after switching on the device, one or several digital video cameras on the outside of the shield make video and continuously sends the image to the computing device. The computing device and the software running on it send the video image frame by frame to the artificial intelligence application. An artificial intelligence application processes each frame using pattern recognition algorithms, identifying the welding arc if present. Changes the resulting image, replaces the welding arc with an illuminated spot that is comfortable for the eye. Comfort is explained by the fact that a uniform distribution of brightness in the field of view is essential for human working capacity. [Alekseev S. V., Usenko V. R. Gigiena truda. Moscow: Medicina, 1988. Glava 19. URL: nashaucheba.ru/v2562/alekseev_s.v.,usenko_v.r._gigien-a_truda?page=22 (Accessed Oct. 24, 2020)]

At the same time, it is possible to use digital light filters and additional darkening of the overly illuminated area around the welding arc to a level of average illumination in the field of vision, which is comfortable for the welder's eyes. If necessary, the artificial intelligence application provides adjustment of the brightness sensitivity of video cameras, based not on the brightness of the arc, but on a level of average illumination in the field of vision, to form an image of the desired brightness. The welder can adjust the brightness of the entire display to the individual characteristics of the welder's vision using, for example, the adjustment buttons on the welding shield. Further, the artificial intelligence application sends the resulting image through the computing device and the interfaces connected to it to the display for output. The artificial intelligence application could perform this without the usage of artificial intelligence algorithms, but rather by using graphical libraries, providing a wide set of features for working with images, such as the OpenCV library [pypi.org/project/opencv-python/].

Thus, unlike the prototype and known technical solutions, after turning on the welder's shield, the welder always sees a uniformly illuminated screen. As mentioned above, the uniform distribution of brightness in the field of view is essential for human working capacity. [Alekseev S. V., supra] This opportunity improves working conditions. There is no need for the welder to control the movement of the filter using the pressure in the mouth. This feature automatically protects the vision from overloading when a welding arc occurs. Not only a small area around the electric arc is clearly visible, but the entire area of the line of sight. The welder does not need to be interrupted to inspect the area to be welded, to estimate when the end of the soldering line will be reached, what part of the soldering line is done. You don't need to rely on visual memory and evaluate intuitively. These features help to increase labor productivity.

FIG. 1 illustrates a welding shield 100. The system of welding shield includes the frame of the welding shield 110. Frame of the welding shield is fixed on the head of a welder 170.

A power source 120 and computing device 160 are attached to the top of the frame of the welding shield. One or more video cameras 130 are located on the outside of the welder's shield. These video cameras must be resistant to bright light and ultraviolet radiation. Display 140 is located on the inside of the shield in front of the welder's eyes.

An optical system 150 is located on the inside of the shield in front of the display 140. The system allows the welder to adjust the image to the individual characteristics of the welder's vision. It includes two regulators. One regulator allows you to adjust the setting to take into account myopia, hyperopia in both eyes. The second regulator allows you to adjust the setting for the characteristics of one of the eyes, if the eyes have different visual characteristics.

The computing device contains software including a real-time operating system. The real-time operating system ensures that the latency does not exceed a certain amount of time. WindRiver Linux [windriver.com/products/linux/] can be used as a real-time operating system.

The task of detecting images belongs to the field of artificial intelligence. The application operating in the device that detects the occurrence of a welding arc is an artificial intelligence application. There are ready-made libraries that allow you to detect images in applications. The artificial intelligence application can use Mask R-CNN machine learning detector library [https://github.com/matterport/Mask_RCNN] to detect the appearance of a welding arc. Such libraries can use machine learning models based, for example, on neural networks or histogram of oriented An artificial intelligence application can use the OpenCV library [pypi.org/project/opencv-python/] to change the resulting image and replace the welding arc with a bright spot that is comfortable for the eye.

Mask R-CNN model returns four items for each recognized object on the frame:

(1) The integer value of the type of the detected object.

(2) The degree of confidence in the recognition results. The higher the number, the more confident the model is in recognizing the object correctly.

(3) A bounding box for an object in the form of the XY coordinates of pixels in the frame.

(4) A mask which indicates which pixels within the bounding box are part of the object. Using the mask, one can find the outline of an object.

Below is the example of the code for detecting welding arcs using the Mask R-CNN pre-trained model. The notation of Python programming language will be used in example [***.python.org].

```
import mrcnn.config
import mrcnn.utils
from mrcnn.model import MaskRCNN
# the importing of all other required libraries
# a class setting configuration of Mask-RCNN library.
class MaskRCNN_config(mrcnn.config.Config):
    NAME = " pretrained_model_with_welding_arc_config"
    IMAGES_PER_GPU =... #required value
    GPU_COUNT =... #required value
    NUM_CLASSES = ...#required value
    DETECTION_MIN_CONFIDENCE = ...#required value
# Initialize Mask R-CNN model.
model_instance=MaskRCNN(mode="inference",model_dir=MODEL_DIR,config=MaskRCNN_config( ))
# Load Mask R-CNN pre-trained model from permanent storage device.
model.load_weights(COCO_MODEL_PATH, by_name=True)
def check_frame_for_welding_arc( ):
    #obtain current frame
    cur_frame = ...
    # Detecting objects in the frame
    results = model_instance.detect([cur_frame], verbose=0)
    # Mask R-CNN assumes that objects in multiple images are recognized
    # One image passed in this example, so it's need to retrieve only the first result.
    first_result = results[0]
    # The variable first_result now contains the detection results and has next fields:
    # - first_result ['rois'] — a bounding box for each object;
    # - first_result ['class_ids'] — the integer value of the type for each object;
    # - first_result ['scores'] — the degree of confidence for each object;
    # - first_result ['masks'] — a mask for each object.
    for cur_index, cur_box in enumerate(first_result ['rois']):
        # Check if current object is welding arc
        if class_ids[cur_index] == WeldingArcClassId:
            #Welding arc found handle this case
            handle_weldeing_arc_detection( )
``` gradients, depending on the implementation. The detection functionality of Mask R-CNN library is based on convolutional neural network with some additional features for higher performance.

Common Objects In Context dataset [cocodataset.org/#home] is suitable as a training dataset for training a model based on Mask R-CNN. This training set should be extended with marked welding arc images. Also, a new object type should be added to the training dataset for training a model corresponding to the welding arc. In this case, a pre-trained model should be prepared based on the Mask R-CNN with the above dataset. Prepared pre-trained model should be copied to the permanent storage device of the computing device. This model will be used by an artificial intelligence application for detect a welding arc by means of Mask R-CNN library.

In the example above the function MaskRCNNConfig used for set required parameters for Mask R-CNN model. In the example the class instance model_instance is Mask R-CNN model. The function check_frame_for_welding_arc illustrates the way to detect a welding arc with usage of Mask R-CNN and other above-mentioned libraries. The function check_frame_for_welding_arc obtains current frame for handling in the variable cur_frame by some way omitted in the example for simplicity. The call of the function model_instance.detect allows get all detected object in the variable first_result. After the find of welding arc is performed in the cycle throw all detected objects. If welding arc is found, the function handle_welding_arc_detection is called.

It should be noted that the computing device and all its components, including permanent storage device, random access memory, one or more computer processors, and interfaces must have sufficient hardware performance to ensure processing and transmission of video data with a delay visually imperceptible for the welder. Mask R-CNN architecture is designed in such a way that object identification is quite fast. With a modern graphical processing unit (GPU), one can identify objects in high-definition video at a speed of several frames per second. The advantages of the GPU in the performance of objects detection appear when processing high-resolution images. (***.researchgate.net/publication/342575655_CPU_vs_GPS_performace_of_deep_learning_based_face_detectors_using_resized_images_in_forensic_applications) This should be sufficient for these tasks. Thus, the computing device may have a high performance graphical processing unit for fast image processing and identification.

Figure 2:
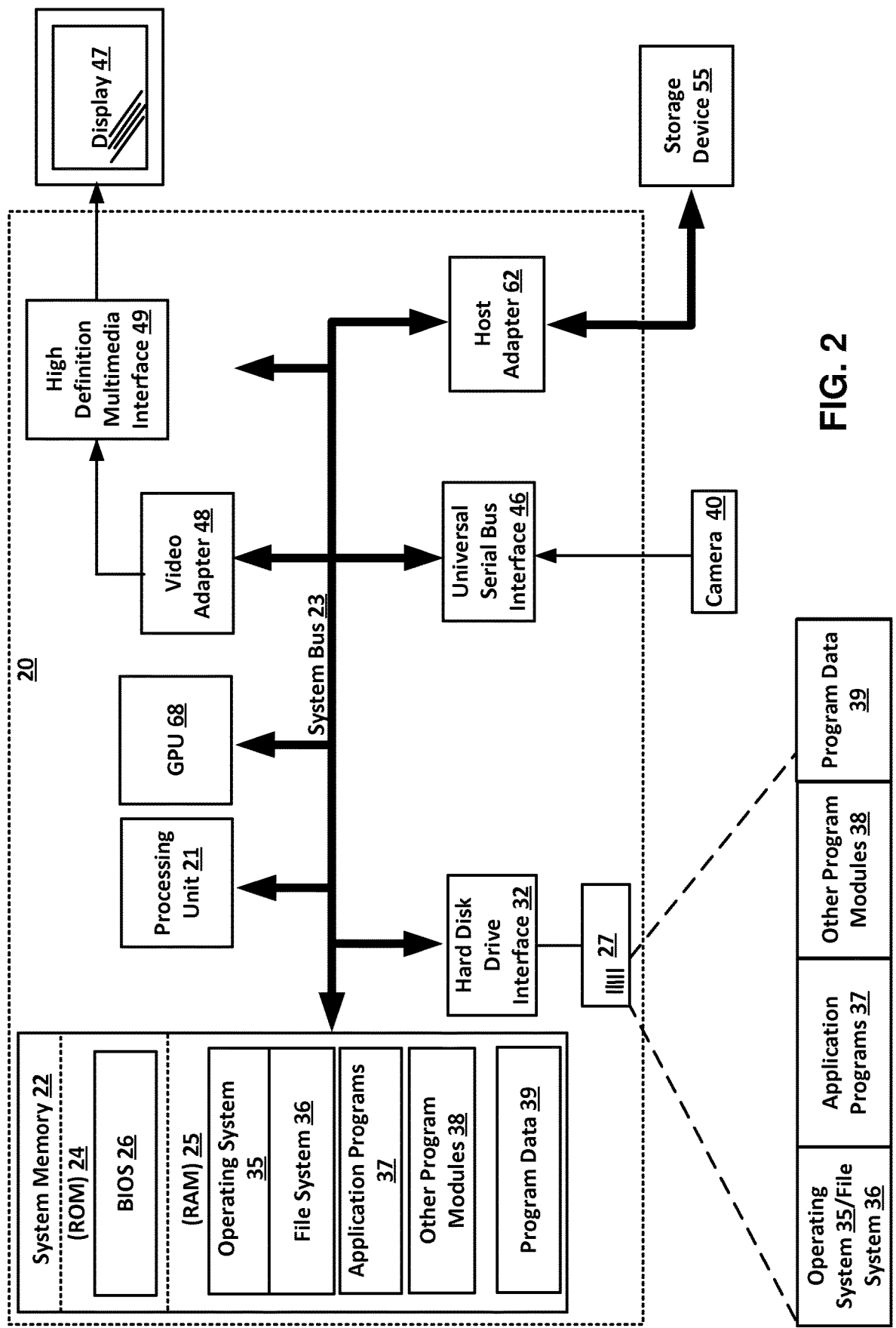
FIG. 2 is an exemplary system architecture.

With reference to FIG. 2, an exemplary system for implementing the invention includes a general purpose computing device in the form of a host computer 20 or the like, including a processing unit (CPU) 21, one or more Graphical Processing Units 68, a system memory 22, and a system bus 23 that couples various system components including the system memory to the processing unit 21.

The system bus 23 may be any of several types of bus structures including a memory bus or memory controller, a peripheral bus, and a local bus using any of a variety of bus architectures. The system memory includes a read-only memory (ROM) 24 and random access memory (RAM) 25. A basic input/output system 26 (BIOS), containing the basic routines that help to transfer information between the elements within the computer 20, such as during start-up, is stored in ROM 24.

The computing device 20 may further include a hard disk drive 27 for reading from and writing to a hard disk, not shown herein. The hard disk drive 27 is connected to the system bus 23 by a hard disk drive interface 32.

The drives and their associated computer-readable media provide non-volatile storage of computer readable instructions, data structures, program modules and other data for the computing device 20. Although the exemplary environment described herein employs a hard disk (storage device 55).

A number of program modules may be stored on the hard disk (storage device 55), ROM 24 or RAM 25, including an operating system 35 (e.g., Android, LINUX or similar) The computing device 20 includes a file system 36 associated with or included within the operating system 35, such as the fourth extended file system (ext4fs) or similar, one or more application programs 37, other program modules 38 and program data 39. A user may switch on/of the computing device 20 with usage of power button (not shown). A host adapter 62 is used to connect to the storage device 55.

A digital video camera 40 and other input devices are often connected to the processing unit 21 through a universal serial bus (USB) interface 46 that is coupled to the system bus, and they may also be connected by other interfaces. A display 47 is also connected to the system bus 23 via a video adapter 48 and an interface, such as a high definition multimedia interface (HDMI) 49. Also, the digital video camera 40 can be connected to the processing unit 21 through a wireless interface, for example, Wi-Fi or BLUETOOTH. Wi-Fi interface use to transmit a data by air. After receiving data by air by means of Wi-Fi interface a data are usually send to the wired interface like HDMI. An example is wireless screen mirroring receiver [any-cast com/blogs/user-manual/m100-user-manual].

Figure 3:
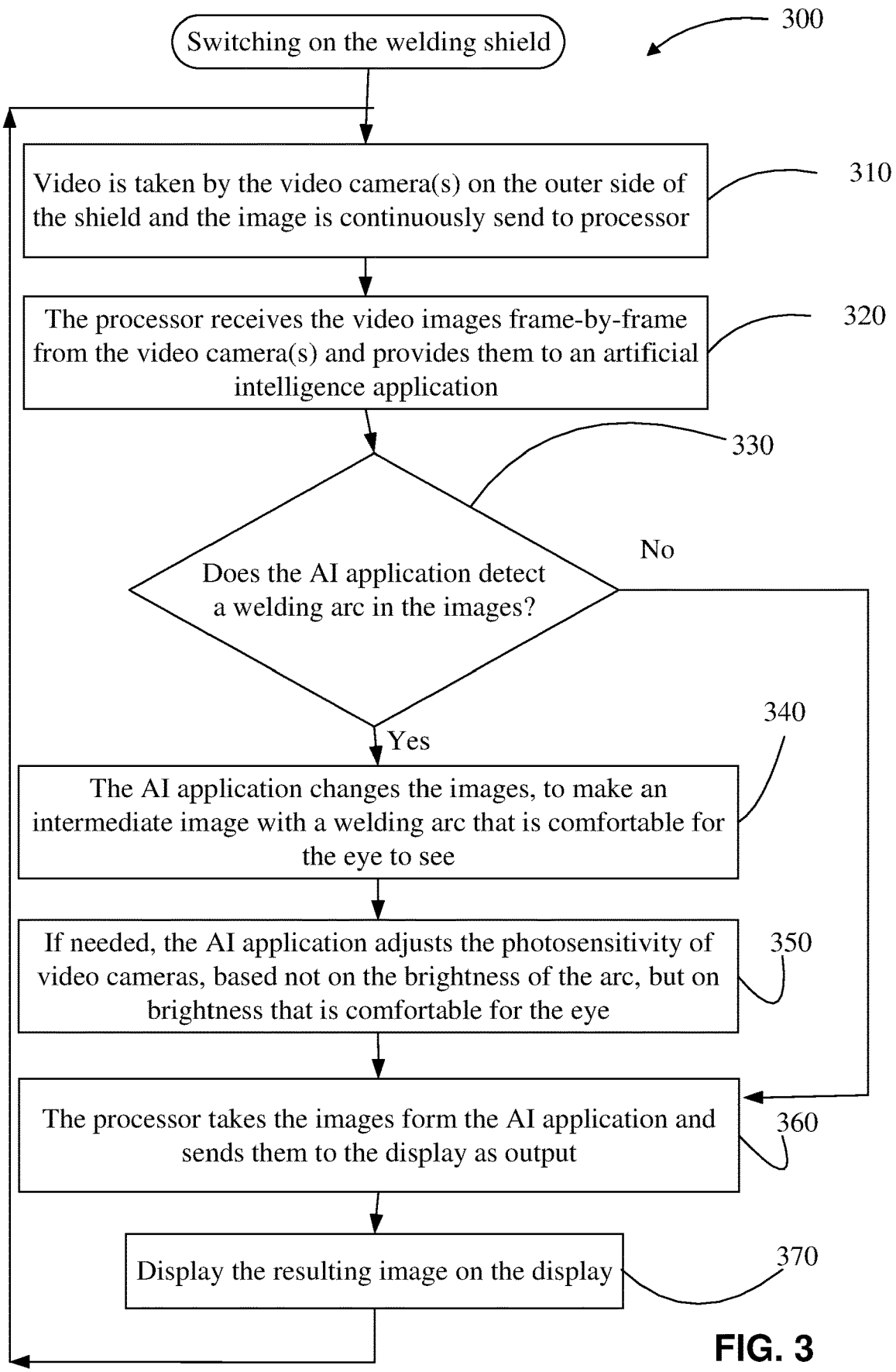
FIG. 3 is a flow chart associated with the operation algorithm of the welder's shield in accordance with this disclosure.

FIG. 3 is a flow chart 300 associated with the operation algorithm of the welder's shield. While the steps shown in FIG. 3 are exemplary operations associated with the present disclosure, variations on the order of the steps, and additional steps, will be apparent to one of skill in the art upon reading the present disclosure.

After switching on the welder's shield video is taken by means of one or more of the mentioned-above video cameras on the outer side of the shield and the image is continuously send to computing device via the mentioned-above interfaces (310) continuously. Further by means of a computing device and software operating on it, video images are received frame-by-frame from mentioned-above one or more video cameras and send to an artificial intelligence application (320). By means of an artificial intelligence application, each video frame is processed using pattern recognition algorithms, and the welding arc is detected if there is one (330). If a welding arc is detected in step 330, by means of an artificial intelligence application, the resulting image is changed, put instead of the welding arc an illuminated spot that is comfortable for the eye, and make by this way an intermediate image (340). Also if necessary, by means of an artificial intelligence application, they provide adjustment of the photosensitivity of video cameras, based, for example, not on the brightness of the arc, but on the brightness that is comfortable for the welder's eye, to form an image of the desired brightness (350). Another option is to adjust the photosensitivity of the camera based on a brightness of the surrounding environment.

By means of an artificial intelligence application, the resulting image is sent through the computing device and the interfaces connected to it to the mentioned-above display for output (360). Step 360 is performed in any case, whether welding arc was detected or not in step 330. At the end of operation cycle device displays the resulting image on the display (370). After step 370 the operation algorithm of the welder's shield moves cyclically to the first step 310 to handle the next video frame.

Also, before sending the processed image to the display in step 360, the artificial intelligence application can combine the data received from infrared and video cameras, and generate using the OpenCV library the resulting image with the highlighting of hot areas with a special range of colors. In this case, information about the temperature comes from one or more infrared cameras. Special colors that characterize the surface temperature are superimposed on the video image before being sent to the display on the inside of the shield. Also, for example, a color scale can be located in the corner of the resulting image, showing the approximate correspondence of color and temperature in the welding area. If there are several digital video cameras in the device, the artificial intelligence application can combine several frames from different video cameras into one resulting image, with goal to obtain advanced characteristics of the result image.

The display can show the battery charge level, the remaining battery time, the current time. A flashing indicator, for example, green, can be displayed in the corner of the display, which signals the correct operation of the device.

Having thus described a preferred embodiment, it should be apparent to those skilled in the art that certain advantages of the described method and apparatus have been achieved. It should also be appreciated that various modifications, adaptations, and alternative embodiments thereof may be made within the scope and spirit of the present invention.

What is claimed is:

1. A welder's shield with artificial intelligence comprising:
   a frame for mounting on a user's head;
   a camera mounted on the frame and directed forward toward a welding zone, so as to obtain images of the welding zone as video data to show to the user;
   a display on an inner side of the frame and integrated into the frame;
   an optical device to enable the user to see the display;
   a processor coupled to a memory;
   a battery providing power to the processor, the display and the camera;
   the processor receiving a video data from the camera;
   the processor running an application to process the video data from the video camera;
   the processor displaying images on the display based on output of the application;
   the processor configured to receive the video data and detecting a welding arc in the welding zone using a pattern recognition algorithm; and
   the processor configured to modify the video data to reduce an intensity of the welding arc in the images that are to be displayed on the display, without reducing an intensity of a remainder of objects in the images being displayed.

2. The shield of claim 1, wherein the video data is provided from the video camera to the processor using a wireless interface.

3. The shield of claim 1, wherein the video data is provided from the video camera to the processor using a high definition multimedia wire interface.

4. The shield of claim 1, wherein the video data is provided from the processor to the display using a high definition multimedia wire interface.

5. The shield of claim 1, wherein the video data is provided to the processor using a universal serial bus wire interface.

6. The shield of claim 1, wherein the processor processes the video data on a frame by frame basis.

7. The shield of claim 1, wherein the pattern recognition algorithm uses a histogram of oriented gradients for detecting the welding arc.

8. The shield of claim 1, wherein the pattern recognition algorithm uses a convolutional neural network for detecting the welding arc.

9. The shield of claim 1, wherein the pattern recognition algorithm uses prepared pre-trained model based on neural network or histogram of oriented gradients, and wherein the model has an object corresponding to the welding arc.

10. The shield of claim 1, wherein the processor provides for adjustment of a photosensitivity of the video camera based on a brightness of the welding arc.

11. The shield of claim 1, wherein the processor provides for adjustment of a photosensitivity of the video camera based on a brightness of a surrounding environment.

12. The shield of claim 1, further comprising a graphical processing unit coupled to the processor for processing the images.

13. A welder's shield with artificial intelligence comprising:
    a frame for mounting on a user's head;
    a camera that obtains images of a welding zone and providing video data to a processor to show to the user;
    a display on an inner side of the frame and integrated into the frame;
    an optical device to enable the user to see the display;
    an image processing application running on the processor for analyzing the video data from the video camera;
    the processor displaying images on the display based on an output of the image processing application;
    the processor configured to detect a welding arc in the welding zone using a pattern recognition algorithm; and
    the processor configured to modify the video data to reduce an intensity of the welding arc in the images that are to be shown on the display, without reducing an intensity of a remainder of objects in the images being displayed.

14. The shield of claim 13, wherein the image processing application uses a convolutional neural network for detecting the welding arc.

15. The shield of claim 13, wherein the image processing application uses prepared pre-trained model based on neural network or histogram of oriented gradients, and wherein the model has an object corresponding to the welding arc.

* * * * *